United States Patent [19]
Ogata et al.

[11] Patent Number: 5,650,404
[45] Date of Patent: Jul. 22, 1997

[54] THERAPEUTIC COMPOSITION FOR PANCREATITIS

[75] Inventors: Kazumi Ogata, Toyonaka; Takahiro Sakaue; Shinya Ogino, both of Itami; Sachiko Matsuura, Osaka; Rie Nagao, Neyagawa, all of Japan

[73] Assignee: Senju Pharmaceutical Co., Ltd., Osaka, Japan

[21] Appl. No.: 503,722

[22] Filed: Jul. 18, 1995

[30] Foreign Application Priority Data

Aug. 5, 1994 [JP] Japan .................. 6-184282

[51] Int. Cl.$^6$ ............................................ A61K 31/665
[52] U.S. Cl. .................... 514/100; 549/220; 549/408
[58] Field of Search ................. 514/100; 549/220, 549/408

[56] References Cited

U.S. PATENT DOCUMENTS

| | | | |
|---|---|---|---|
| 4,564,686 | 1/1986 | Ogata | 549/220 |
| 4,888,329 | 12/1989 | Ogata et al. | 514/100 |
| 4,914,197 | 4/1990 | Yamamoto et al. | 536/117 |
| 4,948,786 | 8/1990 | Shimamoto et al. | 514/100 |

FOREIGN PATENT DOCUMENTS 62-145019  6/1987  Japan .

OTHER PUBLICATIONS

Chicone et al., Medline Abstract 78200271 of "Blood lipid disorders of chronic pancreatitis. 4 cases", Minerva Medica 69 (19), p. 1315 (Apr. 1978).

Steinberg, "Pancreatitis", Cecil Textbook of Medicine, 19th ed., W.B. Saunders Company, pp. 721–727 (1992).

*Primary Examiner*—Jeffrey C. Mullis
*Attorney, Agent, or Firm*—Wenderoth, Lind & Ponack

[57] ABSTRACT

This invention provides a therapeutic composition for pancreatitis which comprises a phosphoric diester compound of the following formula or a pharmacologically acceptable salt thereof

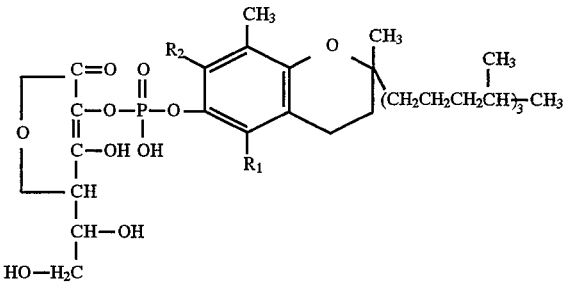

wherein $R_1$ and $R_2$ are the same or different and each represents hydrogen or methyl. The pharmaceutical composition of this invention can be used with advantage in the prevention and treatment of pancreatitis.

1 Claim, No Drawings

THERAPEUTIC COMPOSITION FOR PANCREATITIS

FIELD OF THE INVENTION

This invention relates to a useful therapeutic composition for pancreatitis. More particularly, this invention relates to a useful therapeutic composition for pancreatitis which comprises an ascorbyl tocopheryl phosphate compound or a pharmacologically acceptable salt thereof.

BACKGROUND OF THE INVENTION

In man, there exists not only pancreatic phospholipase $A_2$ ($PLA_2$) (type I) but also membrane-bound and secretion type phospholipase $A_2$ (type II). These types of phospholipase $A_2$ are widely divergent in biochemical properties.

Among them, pancreatic phospholipase $A_2$ is one of the digestive enzymes synthesized in the pancreas and secreted into pancreatic juice. Pancreatic phospholipase $A_2$ is activated by trypsin, a proteolytic enzyme, in the duodenum and decomposes the phospholiplds blended with the bile and solubilized. While pancreatic phospholipase $A_2$ readily decomposes the cell membrane comprised of phospholipids, the lyso compounds produced in this process show high cytotoxicity. Therefore, pancreatic phospholipase $A_2$ has been a focus of attention in connection with the onset and exacerbation of acute pancreatitis. It is generally postulated that since, in man, there is no inhibitor of pancreatic phospholipase $A_2$ activity, pancreatic phospholipase $A_2$ finds its way into the circulation at the acme of pancreatitis to induce severe cytopatic effects. As a drug having such a pharmacologic action, citicholine is known.

Meanwhile, type II phospholipase $A_2$ (non-pancreatic type) which is detected at high levels in the exudates at inflammation sites is generally considered to be deeply involved in inflammation. The mechanism of its inflammatory actions is generally visualized as the type II phospholipase $A_2$-catalyzed production of arachidonic acid from the phospholipids of, for example, the cell membrane which is followed by both the cyclooxygenase pathway leading to prostaglandines (PG) and the lypoxygenase pathway leading to leukotrienes (LT). Steroidal drugs are known to inhibit type II phospholipase $A_2$ and, hence act as antiinflammatory agents blocking both of the pathways.

Thus, type I and type II phospholipase $A_2$ are much different in biochemical properties but in the field of medicine there is not known a drug which sufficiently inhibits both of type I phospholipase $A_2$ which is associated with pancreatitis and type II phospholipase $A_2$ (non-pancreatic type) which is involved in inflammation.

Paying attention to inhibition of pancreatic phospholipase $A_2$, the inventors of this invention did intensive research. As a result, they discovered that an ascorbyl tocopheryl phosphate compound which is already known as an antiinflammatory agent having phospholipase $A_2$ inhibitory activity (U.S. Pat. No. 4,914,197) is of value as a therapeutic drug for pancreatitis by virtue of its pancreatic phospholipase $A_2$ inhibitory action. This invention has been developed on the basis of the above finding.

This invention provides a very useful therapeutic composition for pancreatitis which comprises a phosphoric diester compound or a pharmacologically acceptable salt thereof.

SUMMARY OF THE INVENTION

This invention, therefore, is directed to a therapeutic composition for pancreatitis which comprises a phosphoric diester compound of the following formula or a pharmacologically acceptable salt thereof (hereinafter referred to as the compound)

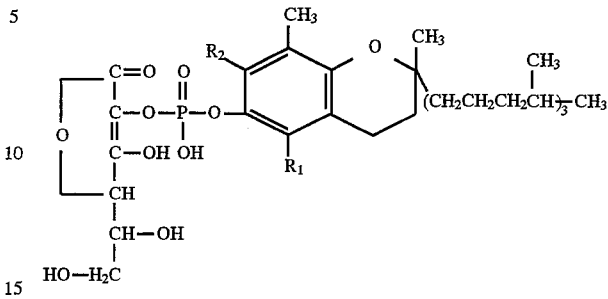

wherein $R_1$ and $R_2$ are the same or different and each represents hydrogen or methyl.

DETAILED DESCRIPTION OF THE INVENTION

The compound for use In the therapeutic composition for pancreatitis according to this invention can be synthesized by the processes described in U.S. Pat. No. 4,564,686 or U.S. Pat. No. 4,914,197, among others.

The compound for use in the therapeutic composition for pancreatitis according to this invention has found application not only as an antiinflammatory drug, referred to above, but also as an anticataract drug, a prophylactic and therapeutic drug for climacteric disturbance, a skin-beautifying cosmetic (U.S. Pat. No. 4,564,686), an antiulcer drug (U.S. Pat. No. 4,888,329) and a prophylactic and therapeutic drug for ischemic disorder in organs (U.S. Pat. No. 4,948,786), among a diversity of uses.

However, even the above-mentioned U.S. Pat. No. 4,914,197 describing the usefulness of this compound as an antiinflammatory drug mentions simply that the compound has activity to inhibit phospholipase $A_2$ of the rat gastric mucosal origin and contains no information at all about its pancreatic phospholipase $A_2$ inhibitory activity which is a useful pharmacologic action for the treatment of pancreatitis. Therefore, it could never be easily conceived of that the very compound might be of use as a therapeutic drug for pancreatitis.

The compound for use in the therapeutic composition for pancreatitis according to this invention may be a free compound or a pharmacologically acceptable salt thereof. The pharmacologically acceptable salt typically includes salts with alkali metals such as sodium, potassium, etc. and salts with alkaline earth metals such as calcium, magnesium, and so on. However, any other salts can likewise be employed only if it is pharmacologically acceptable.

The therapeutic composition for pancreatitis according to this invention may contain one or more species of the present compound according to the intended use and need.

The compound as the active ingredient of the therapeutic composition for pancreatitis according to this invention is a safe compound with only a very low toxic potential and can, therefore, be used for accomplishing the above-mentioned object of this invention [$LD_{50}$ of L-ascorbyl DL-α-tocopheryl phosphate potassium (hereinafter referred to briefly as EPC-K) is $\geq 5$ g/kg p.o. (rats), $\geq 100$ mg/kg i.v. (rats)].

The therapeutic composition of this invention can be administered either orally or parenterally. The dosage form in which the therapeutic composition of this invention can be provided includes solid preparations such as tablets, granules, powders, capsules, etc. and liquid preparations such as injections, all of which can be manufactured by the established pharmaceutical procedures. These dosage forms may contain a variety of additives which are commonly employed, such as excipients, binders, reabsorption promoters, buffers, surfactants, solubilizer, preservatives, emulsifiers, isotonizing agents, stabilizers, pH control agents, etc., each in a suitable amount or proportion.

The dosage of the present compound for use as a therapeutic drug for pancreatitis is dependent on species of the compound, the patient's age, and body weight, clinical manifestations that must be controlled and dosage form, etc. but taking an injection as an example, about 1 mg to about 100 mg per adult man can be administered once a day and in the case of an oral preparation, about 10 mg to about 1,000 mg per adult man be administered a few times a day.

Unless contrary to the spirit and object of this invention, the therapeutic composition of this invention may further contain one or more other therapeutic drugs for pancreatitis and/or other kinds of pharmacologically active ingredients.

EXAMPLES

The following examples and formulation examples are further illustrative of this invention.

Example 1

Effect of the Present Compound on Ethionine-induced Severe Pancreatitis

The therapeutic efficacy of the compound was tested in ethionine-induced pancreatitis which is a model of severe human pancreatitis. The efficacy evaluation was based on the degree of inhibition of the release of amylase into blood which is an indicator of pancreatitis.

Test Substances (1) Investigational Substance

L-Ascorbyl DL-α-tocopheryl phosphate potassium (briefly, EPC-K) 141 mg/10 ml/kg, p.o.

(2) Control Substances

Distilled water 10 ml/kg, p.o.

Camostat monomethanesulfonate (Ono Pharmaceutical) 100 mg/10 ml/kg, p.o.

Animals used: Thirty female BALB/c mice weighing about 18 g as purchased from Japan SLC were used in this experiment. The mice were accommodated in an animal room controlled at 24°±4° C. and 55±15% R. H. and while the animals in the ethionine-induced pancreatitis groups were given low-choline, 0.54 ethionine-supplemented food (prepared by SLC) ad libitum, the animals in the untreated control group were given Labo MR Stock (tradename) (Nihon Nosan Kogyo) ad libitum. Water was freely available for animals in the ethionine pancreatitis groups and the untreated group. The mice were deprived of food 12 hours before commencement of feeding.

Method: Each test substance was administered 12 hours after the beginning of intake of ethionine-supplemented food. Blood sampling was made 24 and 48 hours after the beginning of intake of ethionine-supplemented food and the serum amylase levels were determined.

Results: The results are presented in Table 1.

TABLE 1

Effect of the compound on the elevation of serum amylase in ethionine-induced pancreatitis

| Group | No. of cases | 0 Hr | 24 Hr | 48 Hr |
|---|---|---|---|---|
| Distilled water | 8 | 14023 ± 1383 | 12368 ± 1853 | 41342 ± 16494 |
| EPC-K | 8 | 14573 ± 3132 | 12926 ± 2217 | 16257 ± 9763*1 |
| Camostat monomethane-sulfonate | 7 | 13978 ± 1012 | 12628 ± 1542 | 36288 ± 13921 |
| Untreated | 7 | 13386 ± 1394 | 16376 ± 1558 | 13029 ± 1950*1 |

Each value is the mean ± S.E. All the values are in international units (mU/ml).
Significantly different from the distilled water group:
*1; $p < 0.01$.

As shown in Table 1, the serum amylase level in the distilled water group was not elevated at all till 24 hours after the beginning of intake of ethionine-supplemented food but subsequently rose, significantly as compared with the untreated group, to 41342±16494 (mU/ml) at 48 hours. In the group treated with the compound, the serum amylase level at 48 hours after the beginning of intake of ethionine-supplemented food was 16257±9763 (mU/ml). This level represents a significant inhibition of serum amylase elevation compared with the distilled water group, and is almost within the normal range. On the other hand, the 48-hour amylase level in the group treated with camostat monomethanesulfonate was 36288±13921 (mU/ml), showing no inhibitory effect on amylase elevation.

It is clear from the above results that the present compound is superior to camostat monomethanesulfonate, a commercial therapeutic drug for pancreatitis, in the therapeutic effect on pancreatitis.

Formulation Example 1

Oral Tablet

| | |
|---|---|
| EPC-K | 100 mg |
| Lactose | 75 mg |
| Starch | 20 mg |
| Polyethylene glycol 6000 | 5 mg |

The above ingredients per tablet are mixed in the conventional manner to provide a tablet. Where necessary, the tablet may be sugar-coated.

Formulation Example 2

Injection

| | |
|---|---|
| EPC-K | 200 mg |
| Mannitol | 5.0 g |
| 1N-Sodium hydroxide | q.s. |
| Distilled water | To make 100 ml pH 6.5 |

The above ingredients are mixed and filtered through a bacterial filter in the routine manner. The filtrate is aseptically distributed into glass ampules, 5 ml per ampule, to provide an injection.

The pharmaceutical composition of this invention can be used with advantage in the prevention and treatment of pancreatitis.

What is claimed is:

1. A method for the treatment of pancreatitis by inhibiting pancreatic phospholipase $A_2$ which comprises administering to a patient in need thereof a pharmacologically effective amount of a compound of the formula or a pharmacologically acceptable salt thereof

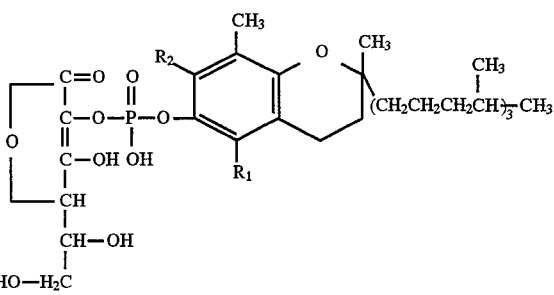

wherein $R_1$ and $R_2$ are the same or different and each represents hydrogen or methyl.

* * * * *